United States Patent
Lu et al.

(10) Patent No.: US 11,549,128 B2
(45) Date of Patent: Jan. 10, 2023

(54) PRETREATMENT METHOD FOR PRODUCING LYCOPENE RAW MATERIAL

(71) Applicant: CHENGUANG BIOTECH GROUP CO., LTD., Hebei (CN)

(72) Inventors: Qingguo Lu, Hebei (CN); Wenjie Han, Hebei (CN); Zhiming Zhang, Hebei (CN); Xiaodong An, Hebei (CN); Wei Gao, Hebei (CN); Qianli Li, Hebei (CN)

(73) Assignee: CHENGUANG BIOTECH GROUP CO., LTD., Hebei (CN)

( * ) Notice: Subject to any disclaimer, the term of this patent is extended or adjusted under 35 U.S.C. 154(b) by 94 days.

(21) Appl. No.: 16/758,957

(22) PCT Filed: Oct. 25, 2017

(86) PCT No.: PCT/CN2017/107705
§ 371 (c)(1),
(2) Date: Apr. 24, 2020

(87) PCT Pub. No.: WO2019/080018
PCT Pub. Date: May 2, 2019

(65) Prior Publication Data
US 2020/0318143 A1 Oct. 8, 2020

(51) Int. Cl.
*C12P 5/02* (2006.01)
(52) U.S. Cl.
CPC ......... *C12P 5/02* (2013.01); *C12Y 302/01004* (2013.01); *C12Y 302/01015* (2013.01)
(58) Field of Classification Search
None
See application file for complete search history.

(56) References Cited

U.S. PATENT DOCUMENTS

| | | | |
|---|---|---|---|
| 5,858,700 A | 1/1999 | Ausich et al. | |
| 5,965,183 A | 10/1999 | Hartal et al. | |
| 9,456,994 B2 | 10/2016 | Sunil Kumar et al. | |
| 9,682,932 B2 | 6/2017 | Joseph et al. | |

FOREIGN PATENT DOCUMENTS

| | | |
|---|---|---|
| CN | 1687239 A | 10/2005 |
| CN | 1775867 A | 5/2006 |
| CN | 1807410 A | 7/2006 |
| CN | 103039437 A | 4/2013 |
| CN | 104938978 A | 9/2015 |
| CN | 105694527 A | 6/2016 |
| WO | 2017084493 A1 | 5/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
English Abstract of CN 103841837 A dated Jun. 4, 2014.
English Abstract of CN 1472183 A dated Feb. 4, 2004.
Huang, Z., "Preservation of Tomato Peel Residue," Xinjiang Animal Husbandry, non-official translation, Dec. 31, 2013, No. 12, pp. 40-41.
PCT International Search Report (Translated) for Intl. App. No. PCT/CN2017/107705 dated Jul. 6, 2018, from which the instant application is based, 2 pgs.

* cited by examiner

*Primary Examiner* — Christian L Fronda
(74) *Attorney, Agent, or Firm* — Fredrikson & Byron, P.A.

(57) ABSTRACT

A pretreatment method for producing a raw material of lycopene, comprising: uniformly mixing tomato peel residue with a fermenting agent, an antioxidant and an enzyme preparation, and subjecting the resultant to light-proof anaerobic fermentation. The present invention employs bacteria-enzyme-combined fermentation technology, which prolongs the storage period of wet tomato peel residue, and also destroys the cell wall of tomato peels, thus facilitating exaction of lycopene and improving the purity of lycopene extracted in the later stage.

11 Claims, No Drawings

PRETREATMENT METHOD FOR PRODUCING LYCOPENE RAW MATERIAL

RELATED APPLICATIONS

This application is a 35 U.S.C. 371 national stage filing from International Application No. PCT/CN2017/107705, filed Oct. 25, 2017, the teachings of which are incorporated herein by reference.

TECHNICAL FIELD

The invention belongs to the field of industrial production of natural plant extracts, and particularly relates to a pretreatment method for a raw material of a natural product, in particular to a pretreatment method for producing a raw material of lycopene.

BACKGROUND ART

Lycopene is a natural pigment contained in plants. It mainly exists in the mature fruits of the tomato which belongs to the family Solanaceae. At present, lycopene is mostly extracted from the tomato pulp, and the tomato peel with high lycopene content is a waste in the production of tomato paste. If the tomato peel could be effectively used, not only could waste be turned into treasure, but also huge social benefits could be created.

However, tomato peel residue is prone to be rotten and spoiled due to its high water content, and thus fresh tomato peel residue needs to be processed immediately when tomato peel residue is used to produce lycopene, otherwise it will become moldy and spoiled. The moldy and spoiled tomato peel residue will cause the loss of lycopene and easy production of harmful substances such as aflatoxin.

SUMMARY OF THE INVENTION

The object of the present invention is to overcome the defects in the prior art and to provide a pretreatment method for producing a raw material of lycopene.

Specifically, the pretreatment method for producing a raw material of lycopene provided by the present invention includes: mixing tomato peel residue with a fermenting agent, an antioxidant, and an enzyme preparation homogenously, and subjecting the resultant to light-proof anaerobic fermentation.

In order to prevent the tomato peel from becoming moldy and spoiled during the storage process, the present invention develops an enzyme-bacteria combined fermentation technology, which completely kills harmful microorganisms in tomato peel residues and thus improves the shelf life of tomato peel residue by inoculation of combined strains and anaerobic fermentation, ensures easier extraction of lycopene by incorporating an enzyme preparation to effectively destroy the cell wall of cells of tomato peel residue, and degrades partial impurities in the tomato peel residue with microorganisms by fermentation, thereby effectively improving the purity of lycopene extracted in the later stage.

The tomato peel residue in the present invention refers to a mixture including tomato peel and tomato seeds which are produced in the process of producing tomato sauce with ordinary tomatoes as a raw material, and the water content of the tomato peel residue is between 50 and 90%.

Specific components and amounts thereof, and fermentation parameters used in the fermentation process are further optimized in the present invention to improve the effect of pretreatment and further improve the purity and extraction efficiency of lycopene. Details are provided below.

The bacterial strain of the fermenting agent used in the present invention is preferably a mixture of *Lactobacillus* and *Bacillus subtilis*, and the ratio of the number of effective viable bacteria of *Lactobacillus* and *Bacillus subtilis* is preferably (2-4):1. In the present invention, instead of simply using *Lactobacillus* to prevent the spoilage of tomato peel residue, a mixture of *Lactobacillus* and *Bacillus subtilis* is used to ferment the tomato peel residue. The *Bacillus subtilis* could quickly deplete the oxygen in the tomato peel residue, and inhibit the growth of other spoilage bacteria, and could produce cellulase to destroy the cell wall of tomato peel, which is more beneficial to the extraction of lycopene. The number of viable bacteria in the fermenting agent is $1 \times 10^{10}$ cfu/g or more, and the additive amount of the fermenting agent is 10 to 20 g/t tomato peel residue, so as to ensure the full interaction between the fermenting agent and tomato peel residue.

The method provided by the present invention adopts an enzyme-bacteria combined fermentation. In order to synergize with the above-mentioned specific strains, the enzyme preparation used in the present invention is preferably a mixture of cellulase, hemicellulase and pectinase, and the weight ratio of the additive amount of cellulose, hemicellulase and pectinase is preferably (2-4):(2-4):1. The total usage amount of the enzyme preparation is 0.5‰ to 2‰ of the weight of tomato peel residue, so as to ensure the full interaction between the enzyme preparation and tomato peel residue.

In the method provided by the present invention, an antioxidant is also added in addition to the fermenting agent and the enzyme preparation. The enzyme preparation would destroy the cell wall of tomato peel, causing the lycopene to be exposed outside of the tomato peel. The present invention could effectively prevent the oxidation of lycopene by adding an antioxidant, thereby improving the yield of lycopene. Specifically, the antioxidant used in the fermentation process is selected from one or a mixture of sodium ascorbate, tea polyphenols, and VE. The additive amount of the antioxidant in the fermentation is 1‰ to 5‰ of the weight of tomato peel residue.

On the basis of optimizing the specific composition and amounts of the above fermenting agent, enzyme preparation and antioxidant, the fermentation in the present invention is preferably carried out at the temperature of 25° C. to 35° C. for a fermentation period of 5 to 10 days, so that the fermentation could be carried out efficiently and smoothly.

In the present invention, the water content of tomato peel residue is preferably controlled to further improve the fermentation effect. Through a lot of practice by the inventor, it is found that the untreated tomato peel residue has a high water content of 80% or more. Under the condition of such water content, it is more beneficial to the growth of spoilage bacteria rather than *Lactobacillus*. By controlling the water content of tomato peel residue to 45% to 65%, preferably about 55% to 65%, it is beneficial to the growth of *Lactobacillus*, and could also inhibit the growth of spoilage bacteria, thereby promoting successful fermentation. The water content of tomato peel residue could be decreased by squeezing before fermentation, which can reduce energy consumption of the subsequent dying. The method for controlling the water content could be conventional dehydration methods in the art, such as squeezing.

In the present invention, it is preferred to add a certain amount of antioxidant to a raw material before the extraction of lycopene, so as to further enable the active ingredient of lycopene in a raw material to be fully extracted and avoid loss by oxidation. The additive amount is preferably 0.5‰ to 2‰ of the weight of a raw material. The specific components of the antioxidant may be the same as or different from the specific components of the antioxidant used during fermentation.

As a preferred embodiment of the present invention, the pretreatment method may include the following specific steps:

(1) squeezing and dehydrating the tomato peel residue; (2) adding the fermenting agent, the antioxidant and the enzyme preparation to the dehydrated tomato peel residue, mixing homogenously, and subjecting the resultant to light-proof anaerobic fermentation; (3) drying the product of fermentation to obtain dried tomato peel residue; (4) separating the peel and the seeds in the dried tomato peel residue to obtain dried tomato peel; (5) crushing the dried tomato peel; (6) mixing the crushed dried tomato peel with an antioxidant and granulating to obtain tomato peel granules as a raw material for producing lycopene.

The product obtained after the pretreatment described in the present invention could be used as a raw material for producing lycopene. The invention also involves a raw material for producing lycopene obtained by the above pretreatment method.

The invention further involves the use of the above a raw material in the production of lycopene.

The method for producing lycopene may be conventional methods in the art, such as a mixed solvent method for extracting lycopene, a supercritical or subcritical method for extracting lycopene and the like, and the present invention is not particularly limited.

Compared with the prior art, the pretreatment method for producing a raw material of lycopene provided by the present invention solves the problem existing in the traditional fermentation in which only a bacterial strain is inoculated for fermentation, adopts the enzyme-bacteria combined fermentation technology, which could prolong the storage period of wet tomato peel residue, destroy the cell wall of tomato peel to facilitate extraction of lycopene, and degrade partial impurities in the tomato peel residue, thereby effectively improving the purity of lycopene extracted in the later stage. In addition, the method provided by the present invention is simple in process and easy to realize industrial production.

SPECIFIC MODES FOR CARRYING OUT THE EMBODIMENTS

The specific embodiments of the present invention will be further described in detail in combination with figures and Examples. The following Examples are intended to illustrate the present invention, but not intended to limit to the scope of the present invention.

Example 1

The present Example provides a pretreatment method for producing a raw material of lycopene, specifically comprising the following steps:

(1) 20 tons of tomato peel residue was squeezed and dehydrated to a water content of 55%;

(2) A composite fermenting agent (in the fermenting agent, the number of effective viable bacteria of *Lactobacillus* was $1\times10^{10}$ cfu/g, and the number of effective viable bacteria of *Bacillus subtilis* was $5\times10^{9}$ cfu/g) was added in an amount of 10 g/t of tomato peel residue to the dehydrated tomato peel residue, a mixed enzyme preparation (in the enzyme preparation, the additive amount of cellulase was 0.2‰, the additive amount of hemicellulase was 0.2‰, and the additive amount of pectinase was 0.1‰) was added in an amount of 0.5‰ of the weight of the peel residue, and a mixture of antioxidants (composed of sodium ascorbate, tea polyphenols, and VE in a weight ratio of 1:1:1) was added in an amount of 1‰ of the weight of the peel residue. After mixing homogenously, the resultant was subpackaged and subjected to anaerobic fermentation in dark at 25° C. for 5 days.

(3) The product obtained in step (2) was dried to obtain dried tomato peel residue.

(4) The peel and the seeds in the dried tomato peel residue were separated to obtain dried tomato peel.

(5) The dried tomato peel was crushed.

(6) The crushed dried tomato peel was added with the mixture of antioxidants used in step (2) in an amount of 0.3‰, the resultant was granulized to obtain tomato peel granules as a raw material for producing lycopene.

Example 2

The present Example provides a pretreatment method for producing a raw material of lycopene, specifically comprising the following steps:

(1) 40 tons of tomato peel residue was squeezed and dehydrated to a water content of 60%.

(2) A composite fermenting agent (in the fermenting agent, the number of effective viable bacteria of *Lactobacillus* was $3\times10^{10}$ cfu/g, and the number of effective viable bacteria of *Bacillus subtilis* was $1\times10^{10}$ cfu/g) was added in an amount of 15 g/t of tomato peel residue with the dehydrated tomato peel residue, a mixed enzyme preparation (in the enzyme preparation, the additive amount of cellulase was 0.6‰, the additive amount of hemicellulase was 0.4‰, and the additive amount of pectinase was 0.2‰) was added in an amount of 1.2‰ of the weight of the peel residue, and tea polyphenol as an antioxidant was added in an amount of 3‰ of the weight of the peel residue. After mixing homogenously, the resultant was subpackaged and subjected to anaerobic fermentation in the dark at 30° C. for 7 days.

(3) The product obtained in step (2) was dried to obtain dried tomato peel residue.

(4) The peel and the seeds in the dried tomato peel residue were separated to obtain dried tomato peel.

(5) The dried tomato peel was crushed.

(6) The crushed dried tomato peel was added with the mixture of antioxidants used in step (2) in an amount of 0.7‰, the resultant was granulized to obtain tomato peel granules as a raw material for producing lycopene.

Example 3

The present Example provides a pretreatment method for producing a raw material of lycopene, specifically comprising the following steps:

(1) 20 tons of tomato peel residue was squeezed and dehydrated to a water content of 65%.

(2) A composite fermenting agent (in the fermenting agent, the number of effective viable bacteria of *Lactobacillus* was $4\times10^{10}$ cfu/g, and the number of effective viable bacteria of *Bacillus subtilis* was $1\times10^{10}$ cfu/g) was mixed in an amount of 20 g/t of tomato peel residue with the dehydrated tomato peel residue, a mixed enzyme preparation (in the enzyme preparation, the additive amount of cellulase was 0.8‰, the additive amount of hemicellulase was 0.8‰, and the additive amount of pectinase was 0.2‰) was added in an amount of 1.8‰ of the weight of the peel residue, and a mixture of antioxidants (the composition of the antioxidants was the same as that in Example 1) was added in an amount of 5‰ of the weight of the peel residue. After mixing homogenously, the resultant was subpackaged and subjected to anaerobic fermentation in the dark at 35° C. for 10 days.

(3) The product obtained in step (2) was dried to obtain dried tomato peel residue.

(4) The peel and the seeds in the dried tomato peel residue were separated to obtain dried tomato peel.

(5) The dried tomato peel was crushed.

(6) The crushed dried tomato peel was added with the mixture of antioxidants used in step (2) in an amount of 1‰, the resultant was granulized to obtain tomato peel granules as a raw material for producing lycopene.

Example 4

The present Example provides a pretreatment method for producing a raw material of lycopene, which is the same as that of Example 3 except that the fermenting agent was formed by mixing *Lactobacillus* and *Saccharomyces*.

Example 5

The present Example provides a pretreatment method for producing a raw material of lycopene, which is the same as that of Example 3 except that the enzyme preparation did not contain hemicellulase, that is, the enzyme preparation was a mixture of cellulase and pectinase with the same enzyme activity as in Example 3.

Comparative Example 1

A pretreatment method for producing a raw material of lycopene was the same as that of Example 3 except that no enzyme preparation was used in step (2).

Comparative Example 2

A pretreatment method for producing a raw material of lycopene was the same as that of Example 3 except that no fermenting agent was used in step (2).

Experimental Example 1

A raw material obtained by the pretreatment methods provided in the Examples and Comparative Examples were allowed to stand under the condition of a temperature of 35° C. and a humidity of 50% for 2 days, and the detection results of the content of aflatoxin were shown in Table 1.

TABLE 1

| the content of aflatoxin in a raw material | |
|---|---|
| | Content of aflatoxin (ppb) |
| Example 1 | not detected |
| Example 2 | 8 |
| Example 3 | 5 |
| Example 4 | 120 |
| Comparative Example 2 | 500 |

It can be seen from the results in Table 1 that a raw material obtained by the pretreatment method provided in the present invention in which fermentation with mixed *Lactobacillus* and *Bacillus subtilis* is used have stable properties, and they are not prone to be rotten and spoiled, and suitable for large-scale industrial production. A raw material obtained by the pretreatment methods described in Examples 1 to 3 have the best properties.

Experimental Example 2

A raw material obtained by the pretreatment methods provided in the Examples and Comparative Examples were used to produce lycopene. The production method specifically includes the following steps: the tomato peel residue granules were extracted with acetone 3 times of the volume of the tomato peel residue granules at 40° C. for three times, and the solvent was recovered to obtain lycopene oleoresin.

After calculation, the yield and purity of the lycopene obtained from a raw material provided in the Examples and Comparative Examples were shown in Table 2.

TABLE 2

| yields and color values of lycopene | | |
|---|---|---|
| | Yield (%) | Color value (%) |
| Example 1 | 85 | 150 |
| Example 2 | 89 | 138 |
| Example 3 | 92 | 162 |
| Example 4 | 74 | 85 |
| Example 5 | 69 | 69 |
| Comparative Example 1 | 67 | 75 |
| Comparative Example 2 | 61 | 58 |

It can be seen from the results in Table 2 that a raw material obtained by the pretreatment method provided in the present invention could produce lycopene in high yield, and the resulting lycopene has low content of impurities and high purity. The lycopene produced from a raw material provided by the pretreatment methods described in Examples 1 to 3 has the best quality.

The above contents are only preferred embodiments of the present invention and are not intended to limit the present invention. Any modification, equivalent replacement, improvement and the like made according to the spirit and principle of the present invention should be regarded as within the protection scope of the invention.

What is claimed is:

1. A pretreatment method for tomato peel residue, comprising the following steps:
uniformly mixing tomato peel residue with a fermenting agent, an antioxidant, and an enzyme preparation, and
subjecting the resultant to light-proof anaerobic fermentation, wherein the fermenting agent is a mixture of *Lactobacillus* and *Bacillus subtilis* with a ratio of the number of effective viable bacteria of (2-4):1;
a total number of effective viable bacteria in the fermenting agent is $1 \times 10^{10}$ cfu/g or more, and the additive amount of the fermenting agent is 10 to 20 g/t tomato peel residue;
the enzyme preparation is a mixture of at least cellulase and pectinase; and
a water content of the tomato peel residue is 45% to 65%.

2. The pretreatment method according to claim 1, wherein the enzyme preparation is a mixture of cellulase, hemicellulase and pectinase;
the total usage amount of the enzyme preparation is 0.5% to 2% of the weight of tomato peel residue.

3. The pretreatment method according to claim 1, wherein the antioxidant is selected from one or a mixture of sodium ascorbate, tea polyphenols, and vitamin E, the additive amount of the antioxidant is 1‰ to 5‰ of the weight of tomato peel residue.

4. The pretreatment method according to claim 1, wherein the fermentation temperature is 25° C. to 35° C. and the fermentation time is 5 to 10 days.

5. The pretreatment method according to claim 1, wherein the water content of the tomato peel residue is 55% to 65%.

6. The pretreatment method according to claim 1, comprising the following specific steps:
 (1) squeezing and dehydrating the tomato peel residue;
 (2) adding the fermenting agent, the antioxidant and the enzyme preparation to the dehydrated tomato peel residue, mixing homogenously, and subjecting the resultant to light-proof anaerobic fermentation;
 (3) drying the product of fermentation to obtain dried tomato peel residue;
 (4) separating the peel and the seeds in the dried tomato peel residue to obtain dried tomato peel;
 (5) crushing the dried tomato peel;
 (6) mixing the crushed dried tomato peel with an antioxidant, and granulizing to obtain tomato peel granules as the raw material for producing lycopene.

7. The pretreatment method according to claim 1, wherein the enzyme preparation mixture further contains hemicellulase; the weight ratio of the additive amount of cellulase, hemicellulase and pectinase is (2-4):(2-4):1;
 the total usage amount of the enzyme preparation is 0.5‰ to 2‰ of the weight of tomato peel residue.

8. The pretreatment method according to claim 2, wherein the antioxidant is selected from one or a mixture of sodium ascorbate, tea polyphenols, and vitamin E, the additive amount of the antioxidant is 1‰ to 5‰ of the weight of tomato peel residue.

9. The pretreatment method according to claim 2, wherein the fermentation temperature is 25° C. to 35° C. and the fermentation time is 5 to 10 days.

10. The pretreatment method according to claim 3, wherein the fermentation temperature is 25° C. to 35° C. and the fermentation time is 5 to 10 days.

11. The pretreatment method according to claim 1, wherein the weight ratio of the additive amount of cellulase, hemicellulase and pectinase is (2-4):(2-4):1.

* * * * *